United States Patent [19]
Rathi et al.

[11] Patent Number: 6,117,949
[45] Date of Patent: Sep. 12, 2000

[54] BIODEGRADABLE LOW MOLECULAR WEIGHT TRIBLOCK POLY (LACTIDE-CO-GLYCOLIDE) POLYETHYLENE GLYCOL COPOLYMERS HAVING REVERSE THERMAL GELATION PROPERTIES

[75] Inventors: Ramesh C. Rathi; Gaylen M. Zentner; Byeongmoon Jeong, all of Salt Lake City, Utah

[73] Assignee: Macromed, Inc., Salt Lake City, Utah

[21] Appl. No.: 09/164,865

[22] Filed: Oct. 1, 1998

[51] Int. Cl.$^7$ .................. C08G 63/91; C08L 67/00
[52] U.S. Cl. .......... 525/415; 528/354; 424/425; 424/426; 424/486; 424/501
[58] Field of Search .............. 525/415; 424/425, 424/426, 486, 561; 528/354

[56] References Cited

U.S. PATENT DOCUMENTS

| | | |
|---|---|---|
| 4,438,253 | 3/1984 | Casey et al. . |
| 4,526,938 | 7/1985 | Churchill et al. . |
| 4,652,441 | 3/1987 | Okada et al. . |
| 4,745,160 | 5/1988 | Churchill et al. . |
| 4,938,763 | 7/1990 | Dunn et al. . |
| 5,100,669 | 3/1992 | Hyon et al. . |
| 5,278,202 | 1/1994 | Dunn et al. . |
| 5,324,519 | 6/1994 | Dunn et al. . |
| 5,330,768 | 7/1994 | Park et al. . |
| 5,702,717 | 12/1997 | Cha et al. .................... 424/425 |

FOREIGN PATENT DOCUMENTS

| | | |
|---|---|---|
| 83301856 | 3/1983 | European Pat. Off. . |
| 87112279 | 8/1987 | European Pat. Off. . |
| 2-78629 | of 1990 | Japan . |
| WO 93/24150 | 12/1993 | WIPO . |

OTHER PUBLICATIONS

K.A. Fults and T.P. Johnston, "Sustained–Release of Urease from a Poloxamer Gel Matrix," *J. Parenteral Science & Technology*, 44(2), 1990: 58–65.

T.P. Johnston and S.C. Miller, "Toxicological Evaluation of Poloxamer Vehicles for Intramuscular Use," *J. Parenteral Science & Technology*, 39(2), 1985: 83–88.

T.P. Johnston and S.C. Miller, "Insulin Disposition Following Intramuscular Administration of an Insulin/Polooxamer Gel Matrix," *J. Parenteral Science & Technology*, 43(6), 1989: 279–286.

T.P. Johnston et al., "Sustained Delivery of Interleukin–2 from a Poloxamer 407 Gel Matrix Following Intraperitoneal Injection in Mice," *Pharmaceutical Research*, 9(3), 1992: 425–434.

(List continued on next page.)

*Primary Examiner*—Duc Truong
*Attorney, Agent, or Firm*—Thorpe, North & Western, LLP

[57] ABSTRACT

A water soluble biodegradable ABA- or BAB-type triblock polymer is disclosed that is made up of a major amount of a hydrophobic polymer made of a poly(lactide-co-glycolide) copolymer or poly(lactide) polymer as the A-blocks and a minor amount of a hydrophilic polyethylene glycol polymer B-block, having an overall weight average molecular weight of between about 2000 and 4990, and that possesses reverse thermal gelation properties. Effective concentrations of the triblock polymer and a drug may be uniformly contained in an aqueous phase to form a drug delivery composition. At temperatures below the gelation temperature of the triblock polymer the composition is a liquid and at temperatures at or above the gelation temperature the composition is a gel or semi-solid. The composition may be administered to a warm-blooded animal as a liquid by parenteral, ocular, topical, inhalation, transdermal, vaginal, transurethral, rectal, nasal, oral, pulmonary or aural delivery means and is a gel at body temperature. The composition may also be administered as a gel. The drug is released at a controlled rate from the gel which biodegrades into non-toxic products. The release rate of the drug may be adjusted by changing various parameters such as hydrophobic/hydrophilic componenet content, polymer concentration, molecular weight and polydispersity of the triblock polymer. Because the triblock polymer is amphiphilic, it functions to increase the solubility and/or stability of drugs in the composition.

69 Claims, 6 Drawing Sheets

OTHER PUBLICATIONS

L. Martini et al., "Micellisation and Gelation of Triblock Copolymer of Ethylene Oxide and ε–Caprolactone, $Cl_nE_mCL_n$, in Aqueous Solution," *J. Chem. Soc. Faraday Trans.*, 90(13), 1994: 1961–1966.

T. Matsuda et al., "Angiopeptin as a Potent Inhibitor of Myointimal Hyperplasia: Systemic Injection and Local Administration via Impregnation in a Biodegradable Polymeric Gel," *ASAIO Journal*, 1993: M512–M517.

K. Morikawa et al., "Enhancement of Therapeutic Effects of Recombinant Interelukin 2 on Transplantable Rat Fibrosarcoma by the Use of a Sustained Release Vehicle, Pluronic Gel," *Cancer Research*, 47, 1987: 37–41.

A.S. Sawhney and J.A. Hubbell, "Rapidly Degraded Terpolymers of dl–lactide, glycolide, and ε–caprolactone with increased hydrophilicty by copolymerization with polyether," *J. Biomedical Mat. Res.*, 24, 1990: 1397–1441.

A.S. Sawhney et al., "Bioerodible Hydrogels Based on Photopolymerized Poly(ethylene glycol)–co–poly(αhydroxy acid) Diacrylate Macromers," *Macromolecules*, 26, 1993: 581–537.

L. Youxin and T. Kissell, "Synthesis and Properties of Biodegradable ABA Triblock Copolymers Consisting of poly(L–lactic acid) or poly(L–lactic–co–glycolic acid) A–blocks attached to central poly(oxyethylene) B–blocks," *J. Controlled Release*, 27, 1993: 247–257.

L. Youxin et al., "In–vitro Degradation and Bovine Serum Albumin Release of the ABA Triblock Copolymers Consisting of poly (L(+) lactic acid), or poly (L(+) lactic acid–co–glycolic acid) A–blocks Attached to Central Polyoxyethylene B–Blocks," *J. Controlled Release*, 32, 1994: 121–128.

BIODEGRADABLE LOW MOLECULAR WEIGHT TRIBLOCK POLY (LACTIDE-CO-GLYCOLIDE) POLYETHYLENE GLYCOL COPOLYMERS HAVING REVERSE THERMAL GELATION PROPERTIES

The present invention relates to water soluble, low molecular weight, thermosensitive, biodegradable block copolymers having an high weight percentage of hydrophobic block(s), and their use for parenteral, ocular, topical, transdermal, vaginal, buccal, transmucosal, pulmonary, transurethral, rectal, nasal, oral, or aural administration of drugs. This invention is made possible by the use of thermosensitive biodegradable triblock polymers based on poly (lactide-co-glycolide) or poly(lactide) and polyethylene glycol blocks, which are described in detail hereinafter. The system is based on the discovery that only a select subset of such block copolymers of relatively low molecular weight and relatively high hydrophobic block polymer content exist as clear solutions at, or about, 5° C. to 25° C. in water but, when the temperature is raised to about body temperature (typically 37° C. for humans), spontaneously interact to form semisolid hydrogels (i.e., gels) that contain high percentages of water entrapped within the gel network, yet are substantially insoluble in water.

BACKGROUND OF THE INVENTION AND SUMMARY OF PRIOR ART

Recently, many peptide/protein drugs, effective for a variety of therapeutic applications, have become commercially available through advances in recombinant DNA and other technologies. However, as polypeptides or proteins, their high molecular weight, degradation in the gastrointestinal tract, and short half-life in the body limits their routes of administration to parenteral administrations such as intravenous or intramuscular and subcutaneous injection. Many peptide drugs are of limited solubility and/or stability in conventional liquid carriers and are therefore difficult to formulate and administer. Also, in many cases, numerous administrations are required to get the expected therapeutic effect for an extended period of time. Long-term controlled delivery of such polypeptides or proteins is essential to provide for practical applications of these medications and to utilize advanced biotechnology derived drugs. Another problem is patient compliance. It is often difficult to get a patient to follow a prescribed dosage regimen, particularly when the prescription is for a chronic disorder and the drug has acute side effects. Therefore, it would be highly desirable to provide a system for the delivery of drugs, polypeptide and protein drugs in particular, at a controlled rate over a sustained period of time, without the above mentioned problems, in order to optimize the therapeutic efficacy, minimize the side effects and toxicity, and thereby increase the efficacy and increase patient compliance.

Drug loaded polymeric devices and dosage forms have been investigated for long term, therapeutic treatment of different diseases. An important property of the polymer is biodegradability, meaning that the polymer can break down or degrade within the body to nontoxic components either concomitant with the drug release, or, after all drug has been released. Furthermore, techniques, procedures, solvents and other additives used to fabricate the device and load the drug should result in dosage forms that are safe for the patient, minimize irritation to surrounding tissue, and be a compatible medium for the drug. Currently, biodegradable implantable controlled release devices are fabricated from solid polymers such as polyglycolic acid, polylactic acid, or copolymers of glycolic and lactic acid. Due to the hydrophobic properties of these polymers, drug loading and device fabrication using these materials requires organic solvents, for example, methylene chloride, chloroform, acetic acid or dimethyl formamide. Obviously, due to the toxic nature of some solvents, extensive drying is generally required after this process. In most cases, the final polymeric device is fabricated in a distinct solid shape (e.g., sphere, slab or rod) requiring implantation that is often accompanied by the trauma of a surgical procedure.

Currently, there are few synthetic or natural polymeric materials which can be used for the controlled delivery of drugs, including peptide and protein drugs, because of the strict regulatory compliance requirements, such as biocompatibility, clearly defined degradation pathway, and safety of the degradation products. The most widely investigated and advanced biodegradable polymers in regard to available toxicological and clinical data are the aliphatic poly($\alpha$-hydroxy acids), such as poly(D,L- or L- lactic acid) (PLA) and poly(glycolic acid) (PGA) and their copolymers (PLGA). These polymers are commercially available and are presently being used as bioresorbable sutures. An FDA-approved system for controlled release of leuprolide acetate, the Lupron Depot™, is also based on PLGA copolymers. The Lupron Depot™ consists of injectable microspheres, which release leuprolide acetate over a prolonged period (e.g., about days) for the treatment of prostate cancer. Based on this history of use, PLGA copolymers have been the materials of choice in the initial design of parenteral controlled release drug delivery systems using a biodegradable carrier.

Even though there has been some limited success, these polymers also have problems associated with their physicochemical properties and methods of fabrication. Hydrophilic macromolecules, such as polypeptides, cannot readily diffuse through hydrophobic matrices or membranes of polylactides. Drug loading and device fabrication using PLA and PLGA often requires toxic organic solvents, and the solid dosage form may mechanically induce tissue irritation.

A. S. Sawhney and J. A. Hubbell, J. Biomed. Mat. Res., 24, 1197–1411 (1990), synthesized terpolymers of D,L-lactide, glycolide and c-caprolactone which degrade rapidly in vitro. For example, a terpolymer composition of 60% glycolide, 30% lactide, and 10% ε-caprolactone exhibited a half-life of 17 days. The hydrophilicity of the material was increased by copolymerization with a poloxamer surfactant (Pluronic F-68). This poloxamer is a block copolymer comprising about 80% by weight of a relatively hydrophobic poly(oxypropylene) block and 20% by weight of a hydrophilic poly(oxyethylene) block. Copolymerization with the poloxamer resulted in a stronger and partly crystalline material which was mechanically stable at physiological temperatures (e.g. 37° C.) in water. The half-life of this copolymer was slightly increased compared to the base polymer. However, it is known that poloxamer-type surfactants are not biodegradable.

An optimum material for use as an injectable or implantable polymeric drug delivery device should be biodegradable, compatible with hydrophilic or hydrophobic drugs, and allow fabrication with simple, safe solvents, such as water, and not require additional polymerization or other covalent bond forming reactions following administration.

One system, which can be fabricated in aqueous solution, is a class of block copolymers referenced above and marketed under the Pluronic™ tradename. These copolymers are composed of two different polymer blocks, i.e. hydrophilic poly(oxyethylene) blocks and hydrophobic poly(oxypropylene) blocks to make up a triblock of poly(oxyethylene)-poly(oxypropylene)-poly(oxyethylene). The triblock copolymers absorb water to form gels which exhibit reverse thermal gelation behavior. However, the Pluronic™ system is nonbiodegradable and the gel properties (water soluble gel) and drug release kinetics (very rapid) from those gels have not proven useful and are in need of substantial improvement.

There is a strong need for hydrophilic biodegradable materials which can be used to incorporate water soluble polypeptide drugs in solution. A. S. Sawhney et al., Macromolecules, Vol 26, No. 4, 581–589 (1993) synthesized macromers having a polyethylene glycol central block, extended with oligomers of $\alpha$-hydroxy acids such as oligo(D,L-lactic acid) or oligo(glycolic acid) and terminated with acrylate groups. Using nontoxic photoinitiators, these macromers can be rapidly polymerized with visible light. Due to the multifunctionality of the macromers, polymerization results in the formation of crosslinked gels. The gels degrade upon hydrolysis of the oligo($\alpha$-hydroxy acid) regions into polyethylene glycol, the $\alpha$-hydroxy acid, and oligo(acrylic acid), and their degradation rates can be tailored by appropriate choice of the oligo($\alpha$-hydroxy acid) from less than 1 day to up to 4 months. However, in this system, a photoinitiator, an additional component, is employed as well as an additional covalent bond-forming photocrosslinking reaction. Highly variable person-to-person performance would result with this approach due to interperson differences in skin thickness and opacity.

Okada et al., Japanese Patent 2-78629 (1990), synthesized biodegradable block copolymeric materials by transesterification of poly(lactic acid) (PLA) or poly(lactic acid)/glycolic acid (PLGA) and polyethylene glycol (PEG). The molecular weight range for PLGA was 400 to 5,000 and for PEG, 200 to 2,000. The mixture was heated at 100° C. to 250° C. for 1 to 20 hours under a nitrogen atmosphere. The product was miscible with water and formed a hydrogel; however, it precipitated in water above room temperature. In other words, the water solubility and interpolymer chain interactions changed with temperature. This polymer is similar to the polymers described in the Churchill patents discussed below and is utilized as an aqueous suspension or molded into a solid block for implantation. There is no indication that this polymer exhibits properties of reverse thermal gelation so as to be injected as a solution instead of as a colloidal suspension of polymer.

T. Matsuda, ASAIO Journal, M512–M517 (1993) used a biodegradable polymeric gel to deliver a potent peptidyl antiproliferative agent, angiopeptin, to prevent the myointimal hyperplasia that occurs when a diseased vessel is replaced with an artificial graft or treated by an intravascular device. A highly viscous liquid of a block copolymer composed of poly(lactic acid) and polyethylene glycol (PLA-PEG) block segments was used as an in situ coatable drug carrier. The materials were supplied by Taki Chemical Co., Ltd., Hyogo, Japan. A prolonged slow release of angiopeptin from the polymer gel, consisting of 0.5 g PLA-PEG and 0.5 mg angiopeptin, was observed in vitro over a few weeks when the gel was kept in a buffer solution maintained at 37° C. No early burst release of angiopeptin was observed. Based on these results, the local sustained angiopeptin release from the biodegradable polymeric gel coated onto an injured vessel in vivo was theorized to be effective.

L. Martini et al., J. Chem. Soc., Faraday Trans., 90(13), 1961–1966 (1994) synthesized very low molecular weight ABA type triblock copolymers by incorporating hydrophobic poly($\epsilon$-caprolactone) which is known to be subject to degradation in vivo by hydrolytic chain scission involving the ester linkages and reported the solution properties of the PCL-PEG-PCL block copolymers. Clouding was observed visually when an aqueous solution of the block copolymers was slowly heated. The cloud points of 2 wt % aqueous solutions of the copolymers were 65° C. and 55° C. for PCL-PEG-PCL (450:4000:450) and PCL-PEG-PCL (680:4000:680), respectively. Reversible gelation on cooling solutions of PCL-PEG-PCL (680:4000:680) was observed at critical concentrations and temperatures ranging from 13% at 25° C. to 30% at 80° C. No lower gel/sol transition was observed on further cooling the solutions to 0° C. The in vitro degradation rate of PCL-PEG-PCL (680:4000:680) was very slow. Only about a 20% decrease in molar mass (from GPC) was observed over a 16 week period. Such slow degradation is insufficient for a practical drug delivery vehicle.

Churchill et al, U.S. Pat. Nos. 4,526,938 and 4,745,160 show copolymers that are either self-dispersible or can be made self-dispersible in aqueous solutions. These copolymers are ABA triblock or AB block copolymers composed of hydrophobic A-blocks, such as polylactide (PLA) or poly(lactide-co-glycolide)(PLGA), and hydrophilic B-blocks, such as polyethylene glycol (PEG) or polyvinyl pyrrolidone. Preferably, to be self-dispersible in water without the use of organic solvents, these polymers must contain more than 50% by weight of hydrophilic (B-block) component as compared to hydrophobic (A block) component or, are copolymers where the hydrophobic component (A block) has a weight average molecular weight of less than 5,000. Although polymers having a weight average molecular weight as low as 1000 are mentioned, there is no direct teaching of such polymers, or that ABA type polymers having a molecular weight of less than 5000 are functional. Further, there is no exemplification of ABA type polymers other than high molecular weight polymers having a hydrophobic content of at least 50% by weight. There is no indication that these block copolymers are soluble in aqueous solutions at any temperature without the use of organic solvents, nor is there any indication that drug/polymers can be administered as a solution. Rather, administration is disclosed as a colloidal suspension of the polymer, or, drug/polymer dispersions are freeze dried into a powder and processed by compression molding to form a solid suitable for use as an implantable depot formulation. Aqueous drug/polymer suspensions or dispersions are two phase systems wherein the dispersed polymer phase is suspended in the continuous aqueous phase. Such dispersions are not suitable for use in situations where sterile filtering processes are required to remove bacterial or other toxic particulates, as any such process would also remove the drug/polymer particles and result in subtherapeutic doses. ABA-type block copolymers that are water soluble and thermally gel are not included in the Churchill, et al., patents.

From the above discussion it is to be observed that known thermally reversible gels (e.g., Pluronics™) are not inherently useful as drug delivery systems. Although there are block copolymers that possess reverse thermal gelation properties, these gels lack critical characteristics necessary for control of drug release over a sustained period and present toxicity or biocompatibility issues owing to their non-biodegradability. Thus, while the property of reverse thermal gelation is universally recognized as unique and potentially highly useful in the field of drug delivery, there has yet to be a system developed that possesses the properties necessary for a viable system.

OBJECTS AND SUMMARY OF THE INVENTION

It is an object of the present invention to provide low molecular weight triblock copolymer drug delivery systems that are biodegradable, exhibit reverse thermal gelation behavior, namely, exist as a liquid solution at low temperatures, reversibly form gels at physiologically relevant temperatures, and provide good drug release characteristics.

A further object of this invention is to provide a drug delivery system for the parenteral administration of hydrophilic and hydrophobic drugs, peptide and protein drugs, and oligonucleotides.

Yet another object of this invention is to provide a method for the parenteral administration of drugs in a biodegradable polymeric matrix resulting in the formation of a gel depot within the body from which the drugs are released at a controlled rate.

These and other objects are accomplished by means of a biodegradable ABA- or BAB-type block copolymer having an average molecular weight of between about 2000 and 4990 consisting of about 51 to 83% by weight of an hydrophobic A block consisting of a poly(lactide-co-glycolide) (PLGA) block copolymer or a poly(lactide) (PLA) polymer and about 17 to 49% by weight of a hydrophilic B polymer block consisting of a polyethylene glycol. Polyethylene glycol (PEG) is also sometimes referred to as poly(ethylene oxide) (PEO) or poly(oxyethylene) and the terms can be used interchangeably for the purposes of this invention. In the hydrophobic A-block, the lactate content is between about 30 to 100, preferably between about 30 to 80 mole percent and most preferably between about 50 to 80 mole percent. The glycolate content is between about 0 and 70, preferably between about 20 to 70 mole percent and most preferably between about 20 to 50 mole percent.

Additional objects and advantages of this invention will become apparent from the following summary and detailed description of the various embodiments making up this invention.

As used herein the following terms shall have the assigned meanings:

"Parenteral" shall mean intramuscular, intraperitoneal, intra-abdominal, subcutaneous, and, to the extent feasible, intravenous and intraarterial.

"Gelation temperature" means the temperature at which the biodegradable block copolymer undergoes reverse thermal gelation, i.e. the temperature below which the block copolymer is soluble in water and above which the block copolymer undergoes phase transition to increase in viscosity or to form a semi-solid gel.

The terms "gelation temperature" and "reverse thermal gelation temperature" or the like shall be used interchangeably in referring to the gelation temperature.

"Polymer solution," "aqueous solution" and the like, when used in reference to a biodegradable block copolymer contained in such solution, shall mean a water based solution having such block copolymer dissolved therein at a functional concentration, and maintained at a temperature below the gelation temperature of the block copolymer.

"Reverse thermal gelation" is the phenomena whereby a solution of a block copolymer spontaneously increases in viscosity, and in many instances transforms into a semisolid gel, as the temperature of the solution is increased above the gelation temperature of the copolymer. For the purposes of the invention, the term "gel" includes both the semisolid gel state and the high viscosity state that exists above the gelation temperature. When cooled below the gelation temperature, the gel spontaneously reverses to reform the lower viscosity solution. This cycling between the solution and the gel may be repeated ad infinitum because the sol/gel transition does not involve any change in the chemical composition of the polymer system. All interactions to create the gel are physical in nature and do not involve the formation or breaking of covalent bonds.

"Drug delivery liquid" or "drug delivery liquid having reverse thermal gelation properties" shall mean a polymer solution that contains drug (the drug per se can either be dissolved or colloidal) suitable for administration to a warm-blooded animal which forms a gelled drug depot when the temperature is raised to or above the gelation temperature of the block copolymer.

"Depot" means a drug delivery liquid following administration to a warm-blooded animal which has formed a gel upon the temperature being raised to or above the gelation temperature.

"Gel" means the semi-solid phase that spontaneously occurs as the temperature of the "polymer solution" or "drug delivery liquid" is raised to or above the gelation temperature of the block copolymer.

"Aqueous polymer composition" means either a drug delivery liquid or a gel comprised of the water phase having uniformly contained therein a drug and the biodegradable block copolymer. At temperatures below the gelation temperature the copolymer may be soluble in the water phase and the composition will be a solution. At temperatures at or above the gelation temperature the copolymer will solidify to form a gel with the water phase, and the composition will be a gel or semi-solid.

"Biodegradable" means that the block copolymer can chemically break down or degrade within the body to form nontoxic components. The rate of degradation can be the same or different from the rate of drug release.

"Drug" shall mean any organic or inorganic compound or substance having bioactivity and adapted or used for a therapeutic purpose. Proteins, oligonucleotides, DNA, and gene therapies are included under the broader definition of drug.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated.

"Poly(lactide-co-glycolide)" or "PLGA" shall mean a copolymer derived from the condensation copolymerization of lactic acid and glycolic acid, or, by the ring opening polymerization of a-hydroxy acid precursors, such as lactide or glycolide. The terms "lactide," "lactate," "glycolide" and "glycolate" are used interchangeably.

"Poly(lactide)" or "PLA" shall mean a polymer derived from the condensation of lactic acid or by the ring opening polymerization of lactide. The terms "lactide" and "lactate" are used interchangeably.

Therefore, the present invention is based on the discovery that ABA- or BAB-type block copolymers, where the A-blocks are a relatively hydrophobic poly(lactide-co-glycolide)(PLGA) or hydrophobic poly(lactide)(PLA) and the B-block is a relatively hydrophilic polyethylene glycol (PEG), having a hydrophobic content of between about 51 to 83% by weight and an overall block copolymer molecular weight of between about 2000 and 4990, exhibit water solubility at low temperatures and undergo reversible thermal gelation at mammalian physiological body temperatures. At such high hydrophobic content it is unexpected that such block copolymers would be water soluble. It is generally taught that any polymer having a hydrophobic content in excess of 50% by weight is substantially insoluble in water and can only be made appreciably soluble in aqueous systems, if at all, when a certain amount of an organic cosolvent has been added.

Therefore, basic to the present invention is the utilization of ABA- or BAB-type block copolymers having hydrophobic $PL(G)_{z-1}A$ A-block segments and hydrophilic PEG B-block segments according to the formula:

or

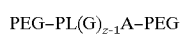

wherein z is an integer of 1 or 2. The block copolymers that have utility as disclosed in this invention meet the criteria summarized in Table 1, namely, compositional make-up within the indicated ranges that result in block copolymers that demonstrate the desired reverse thermal gelling behavior. For purposes of disclosing molecular weight parameters, all reported molecular weight values are based on measurements by NMR or GPC (gel permeation chromatography) analytical techniques. The reported weight average molecular weights and number average molecular weights were determined by GPC and NMR respectively. The reported lactide/glycolide ratio was calculated from NMR data. GPC analysis was performed on a Styragel HR-3 column calibrated with PEG using RI detection and chloroform as the eluent, or on a combination of Phenogel, mixed bed, and Phenogel, 500 Å columns calibrated with PEG using RI detection and tetrahydrofuran as the eluent. NMR spectra were taken in $CDCl_3$ on a Bruker 200 MHz instrument.

TABLE 1

| | |
|---|---|
| Total weight average molecular weight: | 2000 to 4990 |
| PEG content: | 17 to 49% by weight |
| Total PLGA or PLA content: | 51 to 83% by weight |
| Lactate content: | 30 to 100 mole percent |
| Glycolate content: | 0 to 70 mole percent |
| Behavior: | ▶ water soluble below the gelation temperature; |
| | ▶ gels above the gelation temperature |

The biodegradable, hydrophobic A-block segments are poly(α-hydroxy acids) derived or selected from the group consisting of poly(D,L-lactide-co-glycolide), poly(L-lactide-co-glycolide), poly(D,L-lactide), and poly(L-lactide) which are referred to as poly(lactide-co-glycolide)and poly (lactide), respectively, in the present invention. Calculating from the values for total molecular weight and percent by weight PLGA or PLA as given in Table 1, and assuming that the weight average molecular weight of each of the A-blocks in an ABA triblock copolymer or the B-blocks in a BAB triblock copolymer are essentially the same, the weight average molecular weight of each poly(lactide-co-glycolide) or poly(lactide) polymeric A block is between about 600 and 3000.

By similar calculations, the hydrophilic B-block segment is preferably polyethylene glycol (PEG) having an average molecular weight of between about 500 and 2200.

The ABA triblock copolymer may be synthesized by ring opening polymerization, or condensation polymerization according to the following reaction schemes:

SYNTHESIS BY RING OPENING POLYMERIZATION

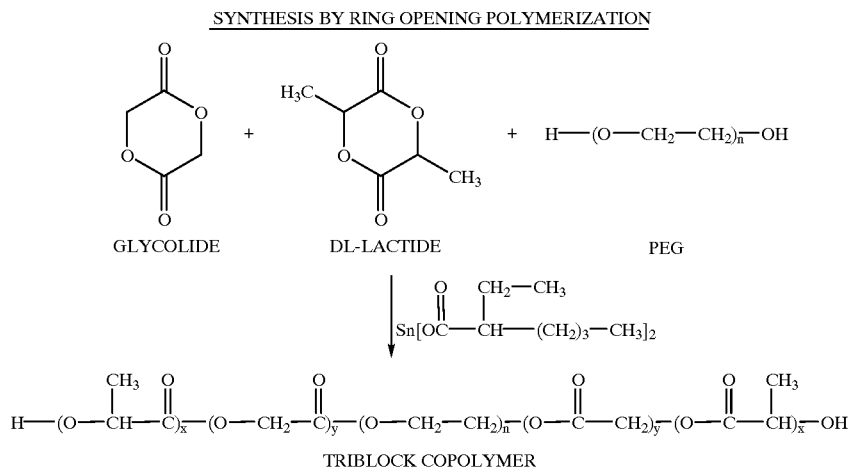

TRIBLOCK COPOLYMER

SYNTHESIS BY CONDENSATION POLYMERIZATION
Step 1: Synthesis of PLGA Oligomer

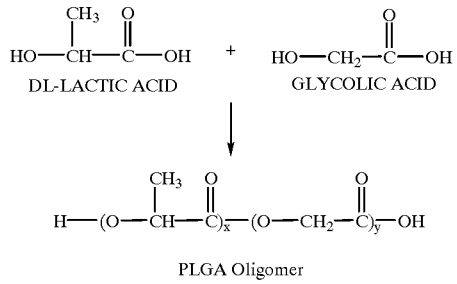

PLGA Oligomer

Step 2: Synthesis of ABA Block copolymer

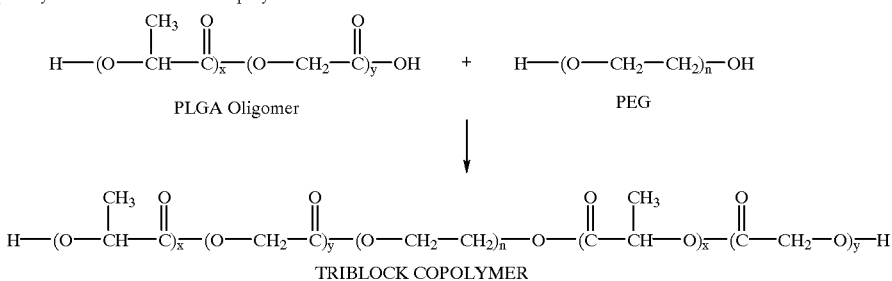

TRIBLOCK COPOLYMER hydrophilic, water-soluble block because of its unique biocompatibility, nontoxicity, hydrophilicity, solubilization properties, and rapid clearance from a patient's body.

The hydrophobic A-blocks are synthesized and utilized because of their biodegradable, biocompatible, and solubilization properties. The in vitro and in vivo degradation of these hydrophobic poly(lactide-co-glycolide) and poly(lactide) A-blocks is well understood and the degradation products are naturally occurring compounds that are readily metabolized and/or eliminated by the patient's body.

Surprisingly, the total weight percentage of the hydrophobic poly(lactide-co-glycolide) or poly(lactide) A-blocks, relative to that of the hydrophilic PEG B-block, is high, e.g. between about 51 to 83% by weight, and most preferably between about 65 to 78% by weight, yet the resulting BAB-type triblock polymers may be similarly formed by appropriate choice of reaction conditions. For example, the B(PEG) blocks may be coupled to the A (PLGA or PLA) blocks by ester or urethane links and the like. Condensation polymerization and ring opening polymerization procedures may be utilized as may the coupling of a monofunctional hydrophilic B block to either end of a difunctional hydrophobic A block in the presence of coupling agents such as isocyanates. Further, coupling reactions may follow activation of functional groups with activating agents such as carbonyl diimidazole, succinic anhydride, N-Hydroxy succinimide and p-nitrophenyl chloroformate and the like.

The hydrophilic B-block is formed from appropriate molecular weights of PEG. PEG was chosen as the triblock polymer retains the desirable water solubility and reverse thermal gelation properties. It is an unexpected discovery that a block copolymer with such a large proportion of hydrophobic component would be water soluble below normal room temperatures such as refrigerator temperatures (5° C.). It is believed the desirable solubility character is possible due to maintaining the overall low molecular weight of the entire triblock copolymer between about 2000 and 4990. Thus, water soluble biodegradable block copolymers possessing thermally reversible gelation properties are prepared wherein the hydrophilic B-block or blocks make up about 17 to 49% by weight of the copolymer and the hydrophobic A-block or blocks make up about 51 to 83% by weight of the copolymer. In a preferred embodiment, the PLGA A-blocks or the PLA A-blocks may comprise between about 65 to 78% by weight of the copolymer and the PEG B-blocks may comprise between about 22 to 35% by weight of the copolymer. Further, the preferred overall average molecular weight of the entire triblock copolymer will be between about 2800 and 4990.

The concentration at which the block copolymers are soluble at temperatures below the gelation temperature may be considered as the functional concentration. Generally speaking, block copolymer concentrations of as low as 3% and of up to about 50% by weight can be used and still be functional. However, concentrations in the range of about 5 to 40% are preferred and concentrations in the range of about 10–30% by weight are most preferred. In order to obtain a viable gel phase transition with the copolymer, a certain minimum concentration, e.g. 3% by weight, is required. At the lower functional concentration ranges the phase transition may result in the formation of a weak gel. At higher concentrations, a strong gel network is formed.

The mixture of the biodegradable copolymer and peptide/protein drugs, and/or other types of drugs, may be prepared as an aqueous solution of the copolymer below the gelation temperature to form a drug delivery liquid where the drug may be either partially or completely dissolved. When the drug is partially dissolved, or when the drug is essentially insoluble, the drug exists in a colloidal state such as a suspension or emulsion. This drug delivery liquid is then administered parenterally, topically, transdermally, transmucosally, inhaled, or inserted into a cavity such as by ocular, vaginal, transurethral, rectal, nasal, oral, buccal, pulmonary or aural administration to a patient, whereupon it will undergo a reversible thermal gelation since body temperature will be above the gelation temperature.

This system will cause minimal toxicity and minimal mechanical irritation to the surrounding tissue due to the biocompatibility of the materials and pliability of the gel, and will completely biodegrade to lactic acid, glycolic acid, and PEG within a specific time interval. The drug release, gel strength, gelation temperature and degradation rate can be controlled by proper design and preparation of the various copolymer blocks, namely, through modifications of the weight percent of the A-blocks and B-blocks, the mole percentages of lactate and glycolate, and the molecular weight and polydispersity of the ABA or BAB triblock copolymers. Drug release is also controllable through adjustment of the concentration of polymer in the drug delivery liquid.

A dosage form comprised of a solution of the block copolymer that contains either dissolved drug or drug as a suspension or emulsion is administered to the body. This formulation then spontaneously gels due to the reverse thermal gelation properties of the block copolymer to form a drug depot as the temperature of the formulation rises to body temperature. The only limitation as to how much drug can be loaded into the formulation is one of functionality, namely, the drug load may be increased until the thermal gelation properties of the copolymer are adversely affected to an unacceptable degree, or until the properties of the formulation are adversely affected to such a degree to make administration of the formulation unacceptably difficult. Generally speaking, it is anticipated that in most instances the drug will make up between about 0.01 to 20% by weight of the formulation with ranges of between about 0.01 to 10% highly common. These ranges of drug loading are not limiting to the invention. Provided functionality is maintained, drug loadings outside of these ranges fall within the scope of the invention.

A distinct advantage to the compositions of the subject invention lies in the ability of the block copolymer to increase the solubility of many drug substances. The combination of the hydrophobic A-block(s) and hydrophilic B-block(s) render the block copolymer amphiphilic in nature. In that regard it functions much as a soap or surfactant in having both hydrophilic and hydrophobic properties. This is particularly advantageous in the solubilization of hydrophobic or poorly water soluble drugs such as cyclosporin and paclitaxel. What is surprising is the degree of drug solubilization of most, if not all, drugs since the major component of the block copolymer is the hydrophobic A-block content. However, as already discussed, even though the hydrophobic polymer block(s) are the major component, the block copolymer is water soluble and it has been found that there is an additional increase in drug solubility when combined in an aqueous phase of the block copolymer.

Another advantage to the composition of the invention lies in the ability of the block copolymer to increase the chemical stability of many drug substances. Various mechanisms for degradation of drugs that lead to a drug's chemical instability have been observed to be inhibited when the drug is in the presence of the block copolymer. For example, paclitaxel and cyclosporin A are substantially stabilized in the aqueous polymer composition of the present invention relative to certain aqueous solutions of these same drugs in the presence of organic co-solvents. This stabilization effect on paclitaxel and cyclosporin A is but illustrative of the effect that would be achieved with many other drug substances.

In certain situations the drug loaded polymer may be administered in the gel state instead of as a solution. The gelation may be the result of raising the temperature of a drug laden polymer solution above the gelation temperature of the polymer prior to administration, or may be caused by raising the concentration of the polymer in the solution above the saturation concentration at the temperature of administration, or may be caused by additives to the polymer solution which causes the solution to gel. In either event, the gel thus formed may be administered parenterally, topically, transdermally, transmucosally, inhaled or inserted into a cavity such as by ocular, vaginal, buccal, transurethral, rectal, nasal, oral, pulmonary or aural administration.

This invention is applicable to bioactive agents and drugs of all types and offers an unusually effective way to deliver polypeptides and proteins. Many labile peptide and protein drugs are amenable to formulation into the block copolymers of the invention and can benefit from the reverse thermal gelation process described herein. While not specifically limited to the following, examples of pharmaceutically useful polypeptides and proteins may be selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-α,β, or γ, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11(IL-11), renin, bradykinin, bacitracins, polymyxins, colistins, tyrocidine, gramicidins, cyclosporins and synthetic analogues, modifications and pharmacologically active fragments thereof, enzymes, cytokines, monoclonal antibodies and vaccines.

The only limitation to the polypeptide or protein drug which may be utilized is one of functionality. In some instances, the functionality or physical stability of polypeptides and proteins can also be increased by various additives to aqueous solutions or suspensions of the polypeptide or protein drug. Additives, such as polyols (including sugars), amino acids, surfactants, polymers, other proteins and certain salts may be used. These additives can readily be incorporated into the block copolymers which will then undergo the reverse thermal gelation process of the present invention.

Developments in protein engineering may provide the possibility of increasing the inherent stability of peptides or proteins. While such resultant engineered or modified proteins may be regarded as new entities in regards to regulatory implications, that does not alter their suitability for use in the present invention. One of the typical examples of modification is PEGylation where the stability of the polypeptide drugs can be significantly improved by covalently conjugating water-soluble polymers such as polyethylene glycol with the polypeptide. Another example is the modification of the amino acid sequence in terms of the identity or location of one or more amino acid residues by terminal and/or internal addition, deletion or substitution. Any improvement in stability enables a therapeutically effective polypeptide or protein to be continuously released over a prolonged period of time following a single administration of the drug delivery liquid to a patient.

In addition to peptide or protein based drugs, other drugs from all therapeutic and medically useful categories may be utilized. These drugs are described in such well-known literature references as the Merck Index, the Physicians Desk Reference, and The Pharmacological Basis of Therapeutics. A brief listing of specific agents is provided for illustration purposes only, and shall not be deemed as limiting: anti-cancer agents such as mitomycin, bleomycin, BCNU, carboplatin, doxorubicin, daunorubicin, methotrexate, paclitaxel, taxotere, actinomycin D and camptothecin; antipsychotics such as olanzapine and ziprasidone; antibacterials such as cefoxitin; anthelmintics such as ivermectin; antivirals such as acyclovir; immunosuppressants such as cyclosporin A (cyclic polypeptide-type agent), steroids, and prostaglandins.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF PREFERRED EMBODIMENTS OF THE INVENTION

Figure 1:
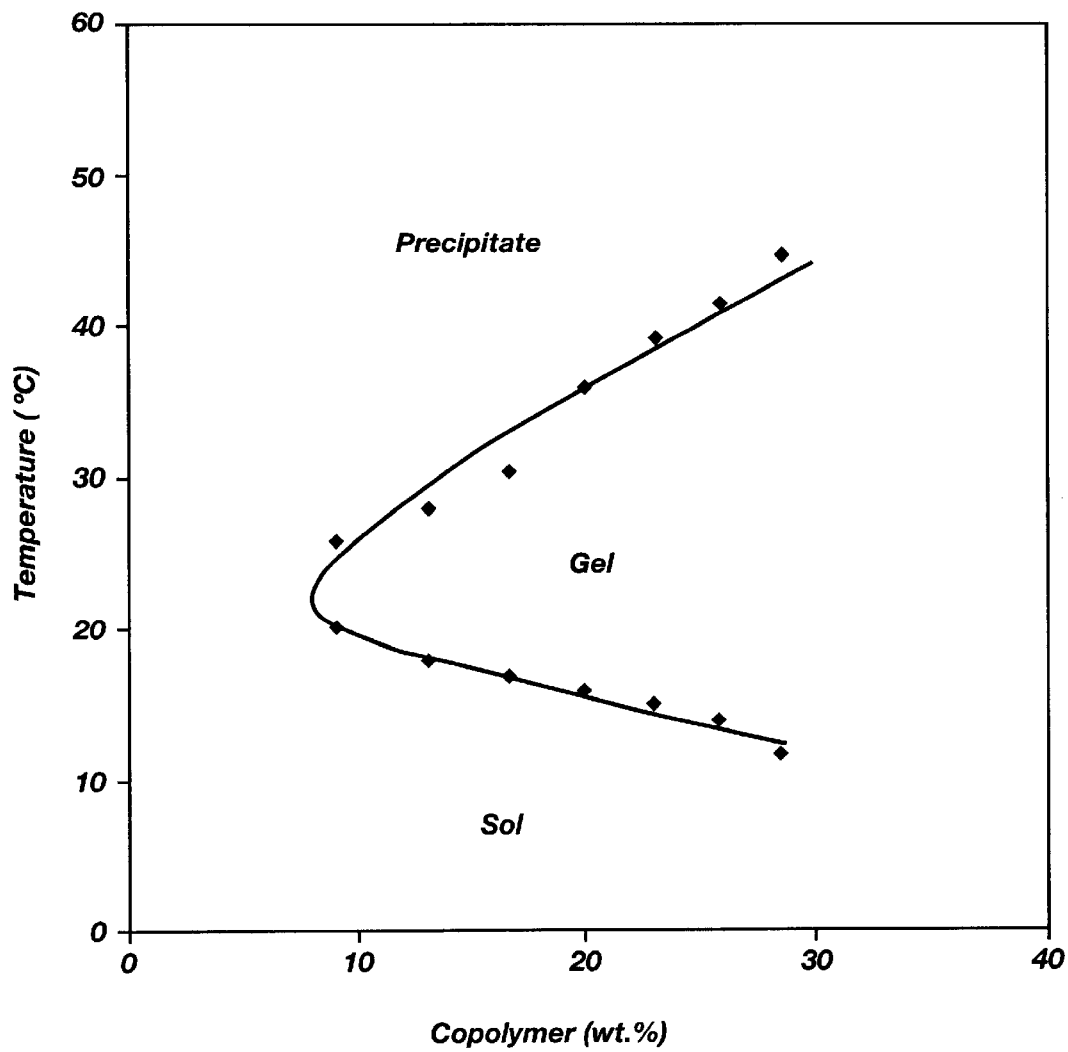
FIG. 1 is a phase diagram illustrating the gelation behavior of aqueous solutions of a PLGA-PEG-PLGA triblock copolymer, studied at different concentrations and temperatures.

In order to illustrate preferred embodiments of this invention, the syntheses of various low molecular weight ABA block copolymers consisting of 64 to 80% by weight hydrophobic A-blocks (poly(lactide-co-glycolide) "PLGA" or poly(lactide) "PLA", and 20 to 36% by weight hydrophilic B-block (polyethylene glycol "PEG") were completed. The object was the preparation of PLGA-PEG-PLGA or PLA-PEG-PLA triblock copolymers having weight average molecular weights of about 2000 to 4990, comprised of two A-blocks each with weight average molecular weights of about 600 to 2000, and a B-block having a weight average molecular weight of about 600 to 2200. Each A-block consists of about 30 to 100 mole percent lactate and 0 to 70 mole percent glycolate.

The following are examples that illustrate preferred embodiments of the invention but are intended as being representative only.

EXAMPLES

Example 1

Synthesis of PLGA-PEG-PLGA Triblock Copolymer by Ring Opening Copolymerization

Following the reaction scheme given above, PEG (Mw=1000) was dried by azeotropic distillation in a flask with toluene (2×75 ml) under an atmosphere of nitrogen followed by drying at 130° C. under vacuum (5 mm Hg). Lactide and glycolide monomers (in mole ratios of 3:1, respectively) were added to the flask followed by the addition of stannous octoate (0.1 wt %) and the reaction mixture was heated at 150° C. under vacuum (5 mm Hg). The progress of the reaction was followed by GPC (gel permeation chromatography). After an appropriate time, the reaction was stopped and the flask was cooled to room temperature. The residue was dissolved in cold water and heated to 70–80° C. to precipitate the polymer formed. The supernatant was decanted and the polymer residue was again dissolved in cold water and heated to induce precipitation. This process of dissolution followed by precipitation was repeated three times. Finally, the polymer was dissolved in a minimum amount of water and lyophilized. The resulting PLGA-PEG-PLGA copolymer had a weight average molecular weight (Mw) of 3737, a number average molecular weight (Mn) of 2928 and an Mw/Mn ratio of 1.3. This copolymer showed reverse thermal gelation properties as more fully detailed in Example 4.

Example 2

Following the basic procedure outlined in Example 1 other triblock copolymers were synthesized using the same PEG (Mw=1000) but varying the lactide and/or glycolide content. The properties of these triblock copolymers are listed in the following table:

Example ABA Block Copolymers with Reverse Thermal Gelation Properties

| GPC Weight Average Molecular Weight | Weight % A-blocks | LA:GA (mole ratio) | Reverse Thermal Gelation |
|---|---|---|---|
| 2052 | 67 | 75:25 | yes |
| 2800 | 64 | 30:70 | yes |
| 3672 | 73 | 75:25 | yes |
| 4000 | 75 | 100:0 | yes |
| 4133 | 76 | 75:25 | yes |
| 4323 | 77 | 50:50 | yes |
| 4920 | 80 | 75:25 | yes |
| 4990 | 80 | 40:60 | yes |

It is to be noted that all of the polymers listed in the above table possessed reverse thermal gelation properties even when the lactide (LA) content varied from 30 to 100 mole % and the glycolide (GA) content varied from 0 to 70 mole %. Hence, both PLGA-PEG-PLGA and PLA-PEG-PLA triblocks are shown in this example.

Example 3

Synthesis of PLGA-PEG-PLGA Triblock Copolymer by Condensation Copolymerization

Into a three necked flask, equipped with a nitrogen inlet, thermometer, and distillation head for removal of water, was placed DL-lactic acid and glycolic acid (3:1 mole ratio, respectively). The reaction mixture was heated at 160° C. under nitrogen with stirring at atmospheric pressure for three hours and then under reduced pressure (5 mm Hg). The progress of the reaction was followed by GPC. The reaction was stopped at the appropriate time and the polymer formed was purified by precipitation from a dichloromethane solution into a large excess of methanol. The residue was triturated with methanol and dried under vacuum (0.05 mm Hg) at 23° C. The PLGA oligomer was characterized by GPC, IR and NMR. The resulting PLGA oligomer had a weight average molecular weight (Mw) of 9900, a number average molecular weight (Mn) of 5500 and an Mw/Mn ratio of 1.8.

The PLGA was mixed with PEG (Mw=1000) and was heated in a flask at 160° C. under a nitrogen atmosphere. The progress of the reaction was followed by GPC. After an appropriate time, the reaction was stopped and the flask was cooled to room temperature. The residue was dissolved in cold water then heated to 70–80° C. to precipitate the copolymer. The supernatant was decanted and the residue was again dissolved in cold water and heated to precipitate the polymer. This process of dissolution and precipitation was repeated three times. Finally, the polymer was dissolved in a minimum amount of water and lyophilized.

The resulting PLGA-PEG-PLGA block copolymer had a weight average molecular weight (Mw) of 4043, a number average molecular weight (Mn) of 2905 and an Mw/Mn ratio of 1.4. The weight average molecular weights and number average molecular weights were determined by GPC and NMR, respectively. The lactide/glycolide ratio was calculated from NMR data. GPC analysis was performed on a Styragel HR-3 column calibrated with PEG using RI detection and chloroform as the eluent. NMR spectra were taken in $CDCl_3$ on a Bruker 200 MHZ instrument. NMR peak assignments confirmed the triblock ABA structure.

Example 4

The gelation behavior of aqueous solutions of the ABA triblock copolymer of Example 1 was studied at different concentrations. Polymer solutions of 9–30% by weight were prepared in water and the change in viscosity was observed at temperatures ranging between 100 and 60° C. Gelation was defined as the physical state where the polymer solution did not readily flow upon inverting a vial of polymer solution. The phase diagram (FIG. 1) of the polymer of Example 1 as a function of temperature and triblock copolymer concentration was generated. The novel, reverse thermal gelation behavior was clearly apparent, and occurred as the triblock copolymer solutions were heated. The gelation at physiologically relevant temperatures (e.g., 37° C.) was particularly prevalent and formed the basis for the substantial utility of the systems for medical and drug delivery purposes.

Example 5

The in vitro degradation of the PLGA-PEG-PLGA triblock copolymer of Example 1 was determined for a 23% by weight solution or gel (1 ml) of copolymer incubated at different temperatures (−10° C., 5° C., 23° C. and 37° C.) and at different initial pH's (3.0, 5.0 and 7.4) over a 30 week period. The degradation and biodegradation of this triblock copolymer was caused by hydrolysis and resulted in lactic acid, glycolic acid and PEG as the final degradation products.

Figure 2A:
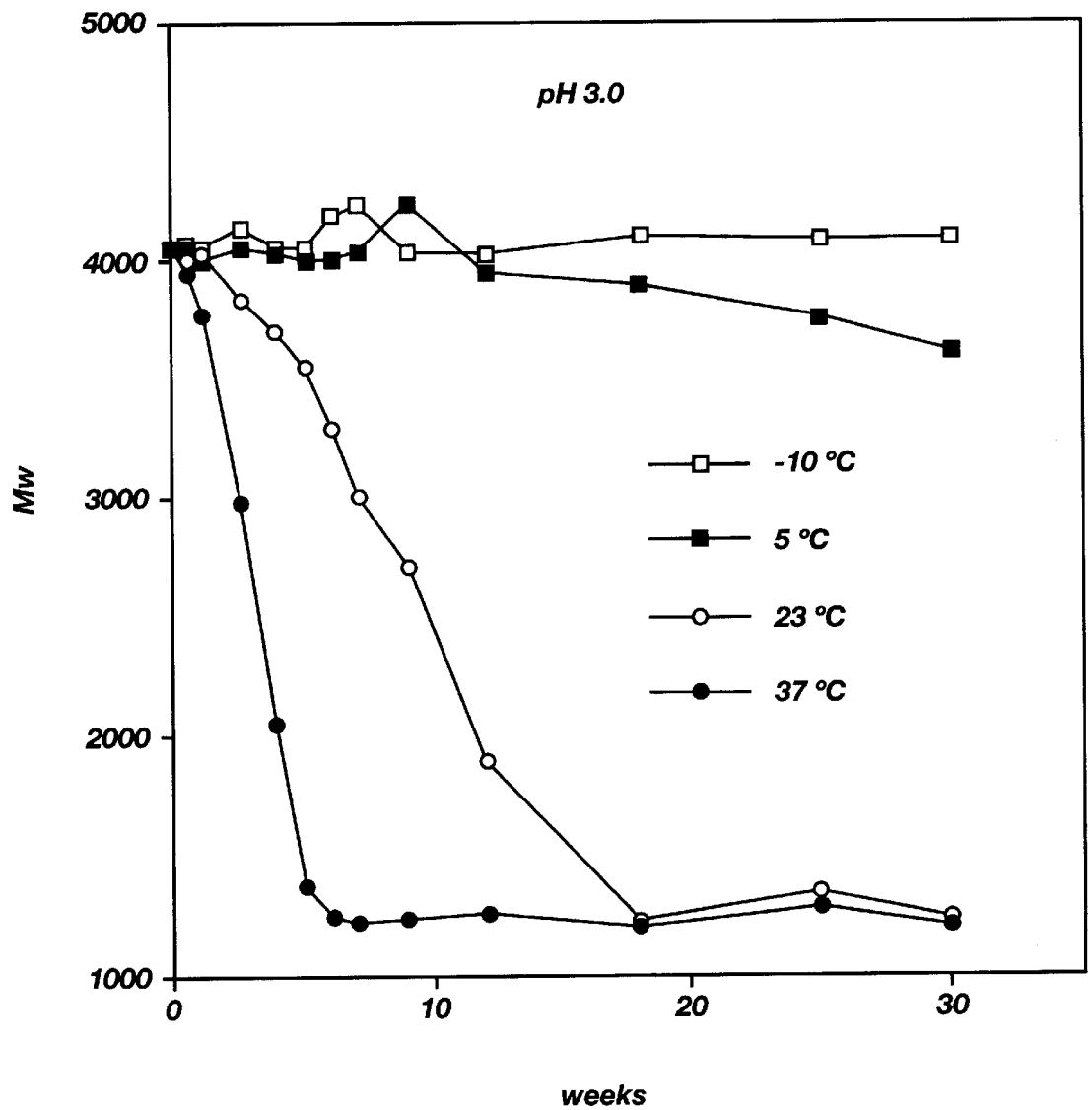
FIGS. 2a–2c are degradation profiles illustrating the in vitro degradation of a PLGA-PEG-PLGA triblock copolymer incubated at different temperatures and pH's.
Figure 2B:
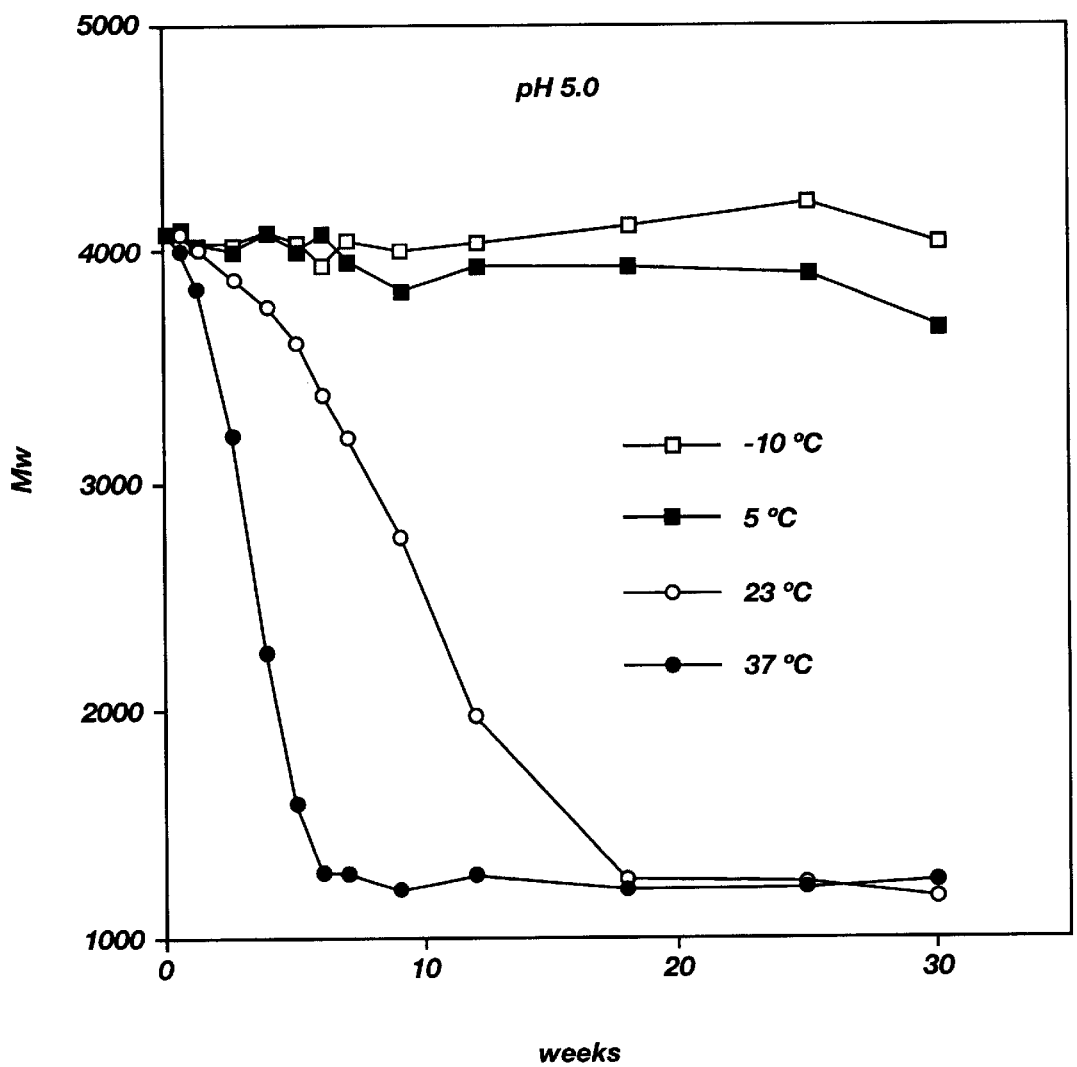
Figure 2C:
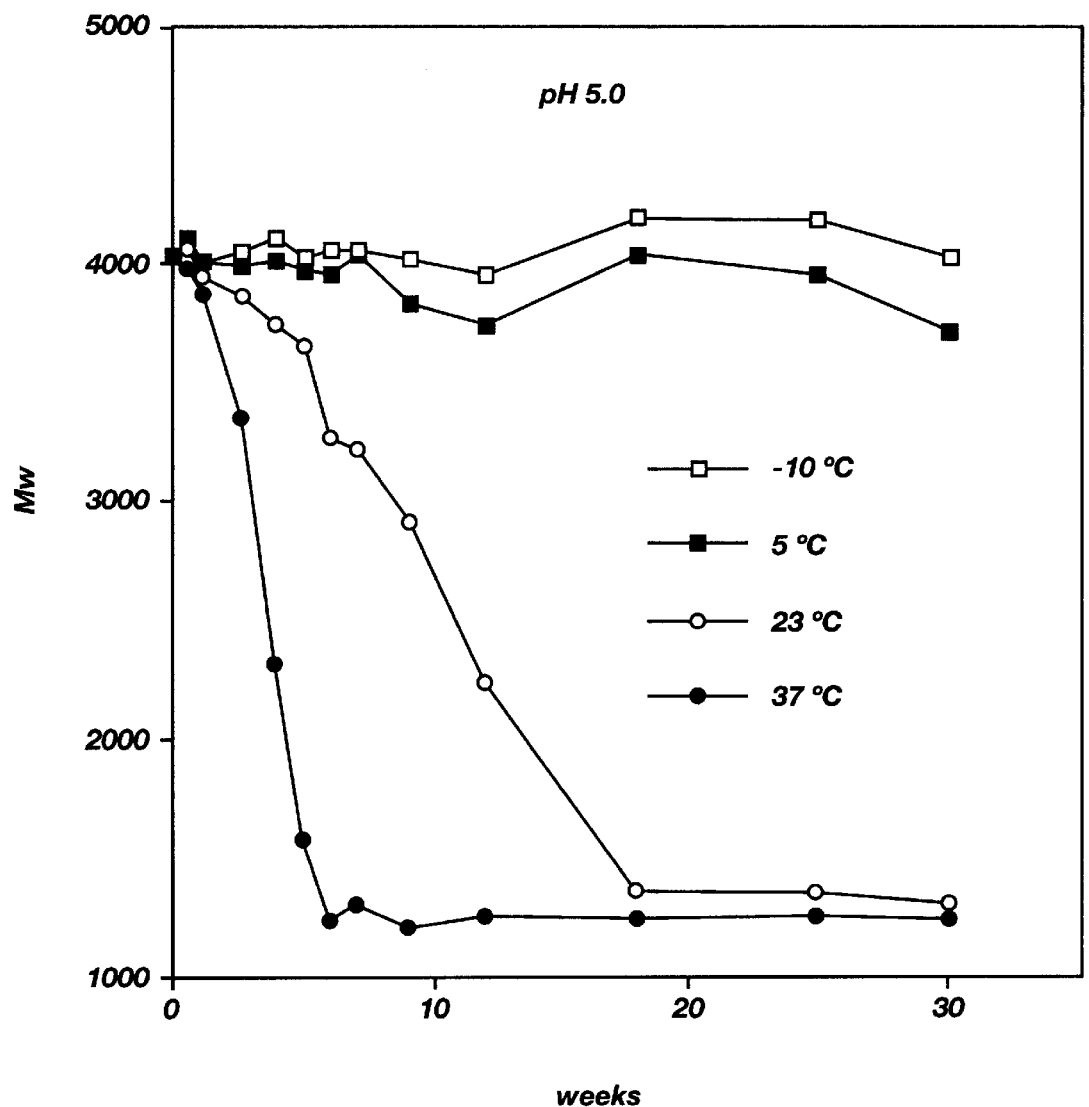

Samples (50 $\mu$l) were taken weekly. The samples were lyophilized, dissolved in chloroform, and the molecular weights of the polymer residues were determined by GPC as described previously. The degradation of the polymer was substantially independent of initial pH over the pH 3.0 to pH 7.4 range which can be attributed to acidification of the media as the polymer hydrolyzed to form lactic acid and glycolic acid. The thermal gelling behavior was also independent of pH over the same pH range. The degradation was more rapid at higher temperatures. The degradation profiles that were generated are shown in FIGS. 2a, 2b and 2c.

Example 6

The in vivo biodegradation of the polymer of Example 1 was determined over a four week period. A 0.40 to 0.45 ml sample of a cold aqueous solution containing 23% by weight triblock copolymer was injected subcutaneously into rats.

Upon reaching body temperature, which was above the gelation temperature of the polymer, a gel lump immediately formed which was visibly apparent. Samples were surgically retrieved as a function of time and indicated that the gel became progressively smaller over a two week period. Between two weeks and four weeks the physical state of the injected triblock copolymer changed from a gel, to a mixture of a gel in a viscous liquid, and finally to a viscous liquid containing no gel that was gradually completely resorbed. At the end of the four week period no formulation was visible at the injection site. Microscopically, small pockets of viscous liquid were observable that also resorbed completely over the following two week period.

Example 7

Paclitaxel and cyclosporin A are hydrophobic drugs that are highly insoluble in water (solubilities were approximately 4 µg/ml). However, these drugs showed significantly higher solubilities when dissolved in aqueous solutions of PLGA-PEG-PLGA triblock copolymer. For example, in a 20% by weight aqueous copolymer solution (polymer of Example 3), paclitaxel was soluble up to 5 mg/ml and cyclosporin A was soluble up to 2 mg/ml.

Paclitaxel and cyclosporin A were highly unstable in aqueous cosolvent solutions (e.g. in water/acetonitrile solutions). The paclitaxel contained in either 20% by weight aqueous PLGA-PEG-PLGA triblock copolymer solutions (i.e., below the gelation temperature of the copolymer) or gels (i.e., above the gelation temperature of the copolymer) was >85% intact after 120 days in storage (5° C. and 37° C.), whereas cyclosporin A was stable over 100 days (5° C.).

Example 8

Figure 3:
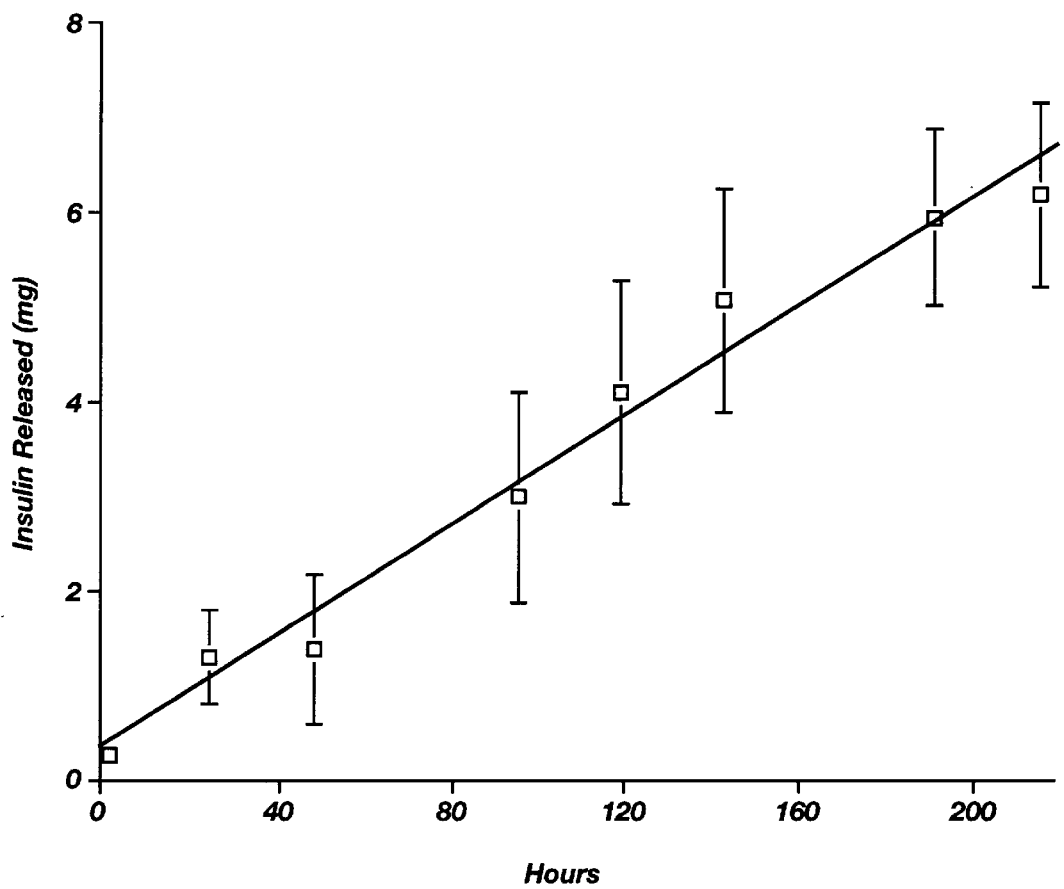
FIG. 3 is a graph illustrating the continuous release of insulin over a sustained period of time from a PLGA-PEG-PLGA triblock copolymer thermal gel.

A 28% by weight aqueous solution of the PLGA-PEG-PLGA triblock copolymer of Example 1 was prepared. Insulin (zinc-free), a parenterally administered protein with proven beneficial effects in the treatment of diabetes mellitus, was suspended in this aqueous solution of triblock copolymer to a final concentration of 5 mg/ml. Approximately 2 ml. of this composition were placed onto a watchglass equilibrated to 37° C. The composition immediately gelled and adhered to the watchglass, whereupon it was placed directly into 10 mM phosphate buffered saline, pH 7.4, 37° C., and the release kinetics of the insulin from the gel were monitored by reversed phase HPLC using UV detection and gradient elution (TFA/acetonitrile/water mobile phase). The data has been graphically summarized in FIG. 3. Insulin was released in a continuous fashion for approximately one week. The utility of the triblock copolymer thermal gel in the controlled delivery of proteins and peptides for a substantial period was clearly established and illustrated by this Example.

Example 9

Figure 4:
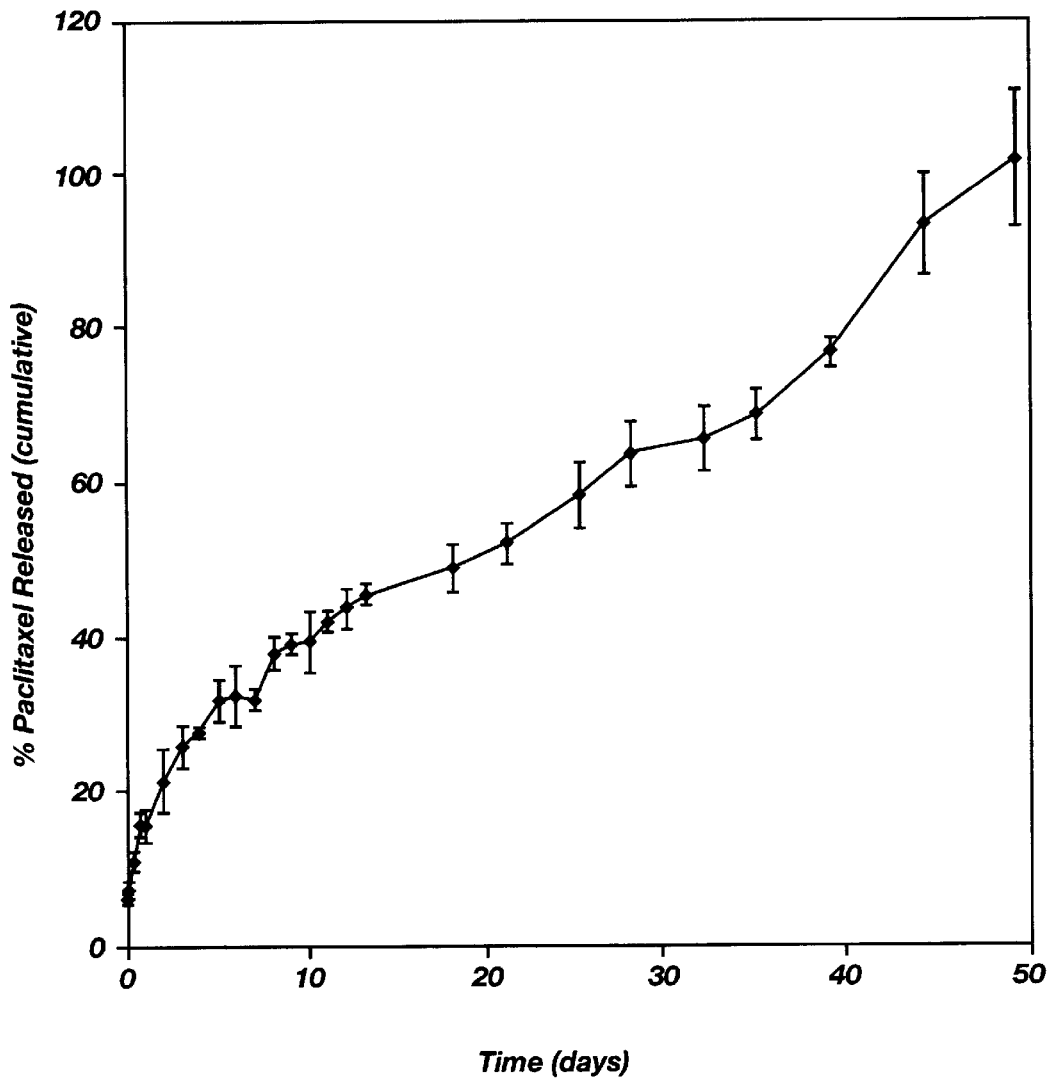
FIG. 4 is a release profile of paclitaxel from a PLGA-PEG-PLGA triblock copolymer thermal gel formulation showing the cumulative controlled release of the paclitaxel for approximately 50 days.

To a 23% by weight aqueous solution of the PLGA-PEG-PLGA triblock copolymer of Example 1 was added sufficient paclitaxel to provide approximately 2.0 mg/ml of drug. A 2 ml sample of this solution was put onto a watchglass and equilibrated at 37° C. Since the temperature was greater than the gelation temperature of the copolymer, a gel formed on the watchglass. The watchglass was placed in a 200 ml beaker containing release media comprised of 150 ml of PBS (pH 7.4) containing 2.4% by weight Tween-80 and 4% by weight Cremophor EL equilibrated at 37° C. The solution in the beaker was stirred. The top of the beaker was sealed to prevent evaporation. The whole assembly was placed into an incubator at 37° C. The release study was performed in triplicate. At different time periods a 5 ml aliquot of the release media was taken and analyzed for paclitaxel. The PBS solution was replaced with fresh PBS after each aliquot removal. Samples were collected at 1, 2, 4, 8, 18, and 24 hours, and thereafter at 24 hour intervals, and analyzed by HPLC. The release profile of paclitaxel from the gel is shown in FIG. 4. The gel formulation provided excellent control over the release of the paclitaxel for approximately 50 days.

Example 10

BAB triblock copolymers were synthesized using the same PEG B-block at either end (Mw=550) but varying the poly(lactide) and/or poly(glycolide) content. The PEG and PLGA were coupled to each other via ester, urethane, or a combination of ester and urethane links. The properties of these triblock copolymers are listed in the following table:

| Example BAB Block Copolymers with Reverse Thermal Gelation Properties | | | |
|---|---|---|---|
| GPC Weight Average Molecular Weight | Weight % A-blocks | PLA:PGA (mole ratio) | Reverse Thermal Gelation |
| 4140 | 70 | 78:22 | yes |
| 4270 | 72 | 78:22 | yes |
| 4580 | 73 | 78:22 | yes |
| 4510 | 73 | 72:28 | yes |

All of the PEG-PLGA-PEG triblock copolymers listed in the above table possessed reverse thermal gelation properties. The sol/gel transition temperatures for the above triblock polymers were 36, 34, 30 and 26° C. respectively.

The above description will enable one skilled in the art to make ABA (e.g., PLGA-PEG-PLGA and PLA-PEG-PLA) or BAB (e.g., PEG-PLGA-PEG and PEG-PLA-PEG) type triblock copolymers that form aqueous solutions having reverse thermal gelation properties and to utilize the same in the field of drug delivery. Although the controlled delivery of both a conventional drug (paclitaxel) and a protein drug (insulin) are illustrated in the examples to show the functionality of hydrogels formed from aqueous solutions of triblock copolymers, these descriptions are not intended to be an exhaustive statement of all drugs which can be utilized and loaded into the biodegradable block copolymers. Certainly, numerous other drugs from various classes of therapeutic agents are well suited for delivery from aqueous compositions of triblock copolymers as described in this description of the invention. Neither are all block copolymers which may be prepared, and which demonstrate the critical reverse thermal gelation property, specifically shown. However, it will be immediately apparent to one skilled in the art that various modifications may be made without departing from the scope of the invention which is limited only by the following claims and their functional equivalents.

We claim:

1. A biodegradable ABA- or BAB-type triblock polymer, said ABA triblock having the formula:

PL(G)$_{z-1}$A–PEG–PL(G)$_{z-1}$A and said BAB triblock having the formula:

PEG–PL(G)$_{z-1}$A–PEG wherein z is an integer of 1 or 2, wherein the A-block is represented by PL(G)$_{z-1}$A such that when z is 2 the A-block is a poly(lactide-co-glycolide) or PLGA copolymer, and when z is 1 the A-block is a poly(lactide) or PLA polymer and wherein the B-block is represented by PEG which is a hydrophilic polyethylene glycol polymer, said block copolymer having a weight average molecular weight of between about 2000 to 4990 and possessing reverse thermal gelation properties, and wherein said PL(G)$_{z-1}$A A-block comprises about 51 to 83% by weight of said polymer and the PEG B-block comprises about 17 to 49% by weight of said polymer.

2. A triblock polymer according to claim 1 wherein the polymer is a BAB type.

3. A triblock polymer according to claim 1 wherein the polymer is a ABA type.

4. A triblock polymer according to claim 3 wherein z is 1 such that the A block is a PLA polymer.

5. A triblock polymer according to claim 3 wherein z is 2 such that the A block is a PLGA copolymer.

6. A triblock polymer according to claim 5 wherein the A-block is a PLGA copolymer comprising between about 80 to 20 mole percent lactide and between about 20 to 80 mole percent glycolide.

7. A triblock polymer according to claim 6 wherein the PLGA A-block comprises between about 65 to 78% by weight and said PEG B-block comprises between about 22 to 35% by weight of said triblock copolymer.

8. A triblock polymer according to claim 6 wherein each PLGA A-block has a weight average molecular weight of between about 600 and 3000 and each PEG B-block has as a weight average molecular weight of between about 500 and 2200.

9. An aqueous biodegradable polymeric drug delivery composition possessing reverse thermal gelation properties comprised of an aqueous phase having uniformly contained therein:

(a) an effective amount of a drug; and (b) a biodegradable ABA- or BAB-type triblock polymer said ABA triblock having the formula:

PL(G)$_{z-1}$A–PEG–PL(G)$_{z-1}$A and said BAB triblock having the formula:

PEG–PL(G)$_{z-1}$A–PEG wherein z is an integer of 1 or 2, wherein the A block is represented by PL(G)$_{z-1}$A such that when z is 2 the A block is a poly(lactide-co-glycolide) or PGLA copolymer, and when z is 1 the A block is a poly(lactide) or PLA polymer and wherein the B block is represented by PEG which is a hydrophilic polyethylene glycol polymer, said triblock polymer having a weight average molecular weight of between about 2000 to 4990, and wherein, in the triblock polymer, the PL(G)$_{z-1}$A A-block comprises about 51 to 83% by weight of said polymer and the PEG B-block comprises about 17 to 49% by weight of said polymer.

10. An aqueous polymeric composition according to claim 9 wherein the triblock polymer content of said composition is between about 3 and 50% by weight.

11. An aqueous polymeric composition according to claim 10 wherein the triblock polymer is a BAB type.

12. An aqueous polymeric composition according to claim 11 wherein the polymer is a ABA type.

13. An aqueous polymeric composition according to claim 12 wherein, in the triblock polymer, z is 1 such that the A-block is a PLA polymer.

14. An aqueous polymeric composition according to claim 12 wherein, in the triblock polymer, z is 2 such that the A-block is a PLGA copolymer.

15. An aqueous polymeric composition according to claim 14 wherein, in the triblock polymer, the A-block is a PLGA copolymer comprising between about 80 to 20 mole percent lactide and between about 20 to 80 mole percent glycolide.

16. An aqueous polymeric composition according to claim 15 wherein, in the triblock polymer, the PLGA A-block comprises between about 65 to 78% by weight and said PEG B-block comprises between about 22 to 35% by weight of said triblock polymer.

17. An aqueous polymeric composition according to claim 15 wherein, in the triblock polymer, each PLGA A-block has a weight average molecular weight of between about 600 and 3000 and each PEG B-block has a weight average molecular weight of between about 500 and 2200.

18. An aqueous polymeric composition according to claim 15 wherein said drug is a polypeptide or protein.

19. An aqueous polymeric composition according to claim 18 wherein said polypeptide or protein is a member selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-α,β, or γ, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof, enzymes, cytokines, monoclonal antibodies and vaccines.

20. An aqueous polymeric composition according to claim 19 wherein the drug content of said composition is between about 0.01 and 20% by weight.

21. An aqueous polymeric composition according to claim 15 wherein said drug is an anti-cancer or anti-cell proliferation agent.

22. An aqueous polymeric composition according to claim 21 wherein said drug is an anti-cancer agent selected from the group consisting of mitomycin, bleomycin, BCNU, carboplatin, doxorubicin, daunorubicin, methotrexate, paclitaxel, taxotere, actinomycin D, and camptothecin.

23. An aqueous polymeric composition according to claim 22 wherein the drug content of said composition is between about 0.01 and 20% by weight.

24. A method for the administration of a drug to a warm blooded animal in a controlled release form which comprises:
(1) providing an aqueous biodegradable polymeric drug delivery composition possessing reverse thermal gelation properties comprised of an aqueous phase having uniformly contained therein:
 (a) an effective amount of a drug; and
 (b) a biodegradable ABA- or BAB-type triblock polymer said ABA triblock having the formula:

$$PL(G)_{z-1}A-PEG-PL(G)_{z-1}A$$

and said BAB triblock having the formula:

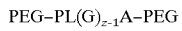
$$PEG-PL(G)_{z-1}A-PEG$$

wherein z is an integer of 1 or 2, wherein the A block is represented by $PL(G)_{z-1}A$ such that when z is 2 the A block is a poly(lactide-co-glycolide) or PLGA copolymer and when z is 1 the A block is a poly(lactide) or PLA polymer and wherein the B block is represented by PEG which is a hydrophilic polyethylene glycol polymer, said block copolymer having a weight average molecular weight of between about 2000 to 4990, and wherein, in the triblock polymer, the $PL(G)_{z-1}A$ A-block comprises about 51 to 83% by weight of said polymer and the PEG B-block comprises about 17 to 49% by weight of said polymer,
(2) maintaining said composition as a liquid at a temperature below the gelation temperature of said triblock polymer; and
(3) administering said composition as a liquid to said warm blooded animal with the subsequent formation of a gel as the temperature of said composition is raised by the body temperature of said animal to be above the gelation temperature of said triblock polymer.

25. A method according to claim 24 wherein said administration is by parenteral, ocular, topical, inhalation, transdermal, vaginal, buccal, transmucosal, transurethral, rectal, nasal, oral, pulmonary or aural means.

26. A method according to claim 25 wherein the triblock polymer content of said composition is between about 3 and 50% by weight.

27. A method according to claim 26 wherein the triblock polymer is a BAB type.

28. A method according to claim 26 wherein the triblock polymer is a ABA type.

29. A method according to claim 28 wherein, in the triblock polymer, z is 1 such that the A-block is a PLA polymer.

30. A method according to claim 28 wherein, in the triblock polymer, z is 2 such that the A-block is a PLGA copolymer.

31. A method according to claim 30, wherein, in the triblock polymer, the A-block is a PLGA copolymer comprising between about 80 to 20 mole percent lactide and between about 20 to 80 mole percent glycolide.

32. A method according to claim 31 wherein, in the triblock polymer, the PLGA A-block comprises between about 65 to 78% by weight and said PEG B-block comprises between about 22 to 35% by weight of said triblock polymer.

33. A method according to claim 32 wherein, in the triblock polymer, each PLGA A-block has a weight average molecular weight of between about 600 and 3000 and each PEG B-block has as a weight average molecular weight of between about 500 and 2200.

34. A method according to claim 31 wherein said drug administered is a polypeptide or protein.

35. A method according to claim 34 wherein said polypeptide or protein is a member selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-α,β, or γ, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof, enzymes, cytokines, monoclonal antibodies and vaccines.

36. A method according to claim 34 wherein the drug content of said composition is between about 0.01 and 20% by weight.

37. A method according to claim 36 wherein said drug administered is an anti-cancer or anti-cell proliferation agent.

38. A method according to claim 37 wherein said drug is an anti-cancer agent selected from the group consisting of mitomycin, bleomycin, BCNU, carboplatin, doxorubicin, daunorubicin, methotrexate, paclitaxel, taxotere, actinomycin D and camptothecin.

39. A method according to claim 37 wherein the drug content of said composition is between about 0.01 and 20% by weight.

40. A method for enhancing the solubility of a drug comprising uniformly admixing an effective amount of said drug in an aqueous biodegradable polymeric drug delivery composition possessing reverse thermal gelation properties said aqueous composition being comprised of an aqueous phase having uniformly contained therein a biodegradable ABA- or BAB-type triblock polymer said ABA triblock having the formula:

$$PL(G)_{z-1}A-PEG-PL(G)_{z-1}A$$

and said BAB triblock having the formula:

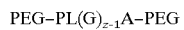
$$PEG-PL(G)_{z-1}A-PEG$$

wherein z is an integer of 1 or 2, wherein the A-block is represented by $PL(G)_{z-1}A$ such that when z is 2 the A-block is a poly(lactide-co-glycolide) or PLGA copolymer, and when z is 1 the A-block is a poly(lactide) or PLA polymer and wherein the B-block is represented by PEG which is a hydrophilic polyethylene glycol polymer, said triblock polymer having a weight average molecular weight of between about 2000 to 4990, and wherein, in the tri-block polymer, the $PL(G)_{z-1}A$ A-block comprises about 51 to 83% by weight of said polymer and the PEG B-block comprises about 17 to 49% by weight of said polymer.

41. A method according to claim 40 wherein the triblock polymer content of said composition is between about 3 and 50% by weight.

42. A method according to claim 41 wherein the triblock polymer is a BAB type.

43. A method according to claim 41 wherein the triblock polymer is a ABA type.

44. A method according to claim 43 wherein, in the triblock polymer, z is 1 such that the A-block is a PLA polymer.

45. A method according to claim 43 wherein, in the triblock polymer, z is 2 such that the A-block is a PLGA copolymer.

46. A method according to claim 45, wherein, in the triblock polymer, the A-block is a PLGA copolymer comprising between about 80 to 20 mole percent lactide and between about 20 to 80 mole percent glycolide.

47. A method according to claim 46 wherein, in the triblock polymer, the PLGA A-block comprises between about 65 to 78% by weight and said PEG B-block comprises between about 22 to 35% by weight of said triblock polymer.

48. A method according to claim 47 wherein, in the triblock polymer, each PLGA A-block has a weight average molecular weight of between about 600 and 3000 and each PEG B-block has as a weight average molecular weight of between about 500 and 2200.

49. A method according to claim 46 wherein said drug is a polypeptide or protein.

50. A method according to claim 49 wherein said polypeptide or protein is a member selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-α,β, or γ, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof, enzymes, cytokines, monoclonal antibodies and vaccines.

51. A method according to claim 49 wherein the drug content of said composition is between about 0.01 and 20% by weight.

52. A method according to claim 46 wherein said drug administered is an anti-cancer or anti-cell proliferation agent.

53. A method according to claim 52 wherein said drug is an anti-cancer agent selected from the group consisting of mitomycin, bleomycin, BCNU, carboplatin, doxorubicin, daunorubicin, methotrexate, paclitaxel, taxotere, actinomycin D and camptothecin.

54. A method according to claim 52 wherein the drug content of said composition is between about 0.01 and 20% by weight.

55. A method for enhancing the stability of a drug comprising uniformly admixing an effective amount of said drug in an aqueous biodegradable polymeric drug delivery composition possessing reverse thermal gelation properties said aqueous composition being comprised of an aqueous phase having uniformly contained therein a biodegradable ABA- or BAB-type triblock polymer said ABA triblock having the formula:

$PL(G)_{z-1}A-PEG-PL(G)_{z-1}A$ and said BAB triblock having the formula:

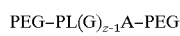

$PEG-PL(G)_{z-1}A-PEG$ wherein z is an integer of 1 or 2, wherein the A-block is represented by $PL(G)_{z-1}A$ such that when z is 2 the A-block is a poly(lactide-co-glycolide) or PLGA copolymer, and when z is 1 the A-block is a poly(lactide) or PLA polymer and wherein the B-block is represented by PEG which is a hydrophilic polyethylene glycol polymer, said triblock polymer having a weight average molecular weight of between about 2000 to 4990, and wherein, in the triblock Polymer, the $PL(G)_{z-1}A$ A-block comprises about 51 to 83% by weight of said polymer and the PEG B-block comprises about 17 to 49% by weight of said polymer.

56. A method according to claim 55 wherein the triblock polymer content of said composition is between about 3 and 50% by weight.

57. A method according to claim 56 wherein the triblock polymer is a BAB type.

58. A method according to claim 58 wherein the triblock polymer is a ABA type.

59. A method according to claim 58 wherein, in the triblock polymer, z is 1 such that the A-block is a PLA polymer.

60. A method according to claim 58 wherein, in the triblock polymer, z is 2 such that the A-block is a PLGA copolymer.

61. A method according to claim 56 wherein, in the triblock polymer, the A-block is a PLGA copolymer comprising between about 80 to 20 mole percent lactide and between about 20 to 80 mole percent glycolide.

62. A method according to claim 61 wherein, in the triblock polymer, the PLGA A-block comprises between about 65 to 78% by weight and said PEG B-block comprises between about 22 to 35t by weight of said triblock polymer.

63. A method according to claim 62 wherein, in the triblock polymer, each PLGA A-block has a weight average molecular weight of between about 600 and 3000 and each PEG B-block has as a weight average molecular weight of between about 500 and 2200.

64. A method according to claim 61 wherein said drug is a polypeptide or protein.

65. A method according to claim 64 wherein said polypeptide or protein is a member selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-$\alpha,\beta$, or $\gamma$, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), HANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof, enzymes, cytokines, monoclonal antibodies and vaccines.

66. A method according to claim 64 wherein the drug content of said composition is between about 0.01 and 20% by weight.

67. A method according to claim 61 wherein said drug administered is an anti-cancer or anti-cell proliferation agent.

68. A method according to claim 67 wherein said drug is an anti-cancer agent selected from the group consisting of mitomycin, bleomycin, BCNU, carboplatin, doxorubicin, daunorubicin, methotrexate, paclitaxel, taxotere, actinomycin D and camptothecin.

69. A method according to claim 67 wherein the drug content of said composition is between about 0.01 and 20% by weight.

* * * * *

UNITED STATES PATENT AND TRADEMARK OFFICE
CERTIFICATE OF CORRECTION

| | |
|---|---|
| PATENT NO. | : 6,117,949 |
| APPLICATION NO. | : 09/164865 |
| DATED | : September 12, 2000 |
| INVENTOR(S) | : Rathi et al. |

It is certified that error appears in the above-identified patent and that said Letters Patent is hereby corrected as shown below:

In Column 1, line 7, insert -- This application is a continuation-in-part of Application Serial Number 08/943,167 filed October 3, 1997, now U.S. Patent No. 6,004,573. --

In Column 20, Line 9, replace "11" with -- 10 --.

In Column 24, Line 36, replace "58" with -- 56 --.

In Column 24, Line 51, replace "35t" with -- 35% --.

Signed and Sealed this

Twenty-ninth Day of July, 2008

JON W. DUDAS
*Director of the United States Patent and Trademark Office*